(12) United States Patent
Clappaz et al.

(10) Patent No.: US 11,730,252 B2
(45) Date of Patent: Aug. 22, 2023

(54) DEVICE FOR DISPENSING A FORMULATION OF AT LEAST TWO COMPOUNDS SELECTED FROM A SET OF SELECTABLE COMPOUNDS AND ASSOCIATED CONTAINER

(71) Applicant: IEVA, Paris (FR)

(72) Inventors: Cyril Clappaz, Eyzin-Pinet (FR); David Moulinier, Lyons (FR)

(73) Assignee: IEVA, Paris (FR)

( * ) Notice: Subject to any disclaimer, the term of this patent is extended or adjusted under 35 U.S.C. 154(b) by 323 days.

(21) Appl. No.: 17/162,250

(22) Filed: Jan. 29, 2021

(65) Prior Publication Data

US 2021/0235846 A1 Aug. 5, 2021

(30) Foreign Application Priority Data

Jan. 31, 2020 (FR) ...................................... 2000948

(51) Int. Cl.
*A45D 40/24* (2006.01)
*B05B 11/00* (2023.01)
(Continued)

(52) U.S. Cl.
CPC .......... *A45D 40/24* (2013.01); *B05B 11/0038* (2018.08); *B05B 11/1084* (2023.01);
(Continued)

(58) Field of Classification Search
CPC ............. A45D 40/24; A45D 2034/005; A45D 2200/056; A45D 34/04; A45D 44/005;
(Continued)

(56) References Cited

U.S. PATENT DOCUMENTS 8,800,818 B2 * 8/2014 Greenberg ............. B65D 83/68
222/266
9,878,339 B2 * 1/2018 Baumann ............ B05B 11/1047
(Continued)

FOREIGN PATENT DOCUMENTS

KR 200440663 Y1 6/2008
WO WO-2010081205 A2 * 7/2010 ............. A45D 34/00
(Continued)

OTHER PUBLICATIONS

Written Opinion issued in FR application No. 20000948, dated Jan. 31, 2020.
(Continued)

*Primary Examiner* — Donnell A Long
(74) *Attorney, Agent, or Firm* — Knobbe, Martens, Olson & Bear LLP

(57) ABSTRACT

A device for dispensing a formulation of at least two compounds selected from a set of selectable compounds includes a plurality of containers storing the different selectable compounds, a pump associated with each container, a dispensing surface that includes at least two through openings configured to convey at least two selected compounds,
(Continued)

a selector configured to connect the at least two through openings to the pumps for the selected compounds and to close the other pumps, and an actuator configured to activate all of the pumps and to only deliver the at least two selected compounds onto the dispensing surface.

10 Claims, 12 Drawing Sheets

(51) Int. Cl.
*B05B 12/14* (2006.01)
*B05B 12/00* (2018.01)
*B05B 11/10* (2023.01)
*A45D 34/00* (2006.01)

(52) U.S. Cl.
CPC ............ *B05B 12/002* (2013.01); *B05B 12/14* (2013.01); *B05B 12/1409* (2013.01); *B05B 12/1472* (2013.01); *A45D 2034/005* (2013.01); *A45D 2200/056* (2013.01)

(58) Field of Classification Search
CPC .......... A45D 2200/058; B05B 11/0038; B05B 11/1084; B05B 12/002; B05B 12/14; B05B 12/1409; B05B 12/1472; B05B 11/0032; A61M 35/003; B01F 33/841
See application file for complete search history.

(56) References Cited

U.S. PATENT DOCUMENTS

| | | | |
|---|---|---|---|
| 2002/0197228 A1* | 12/2002 | LaSala | ................ B05B 11/0072 424/70.12 |
| 2014/0020706 A1* | 1/2014 | Thiebaut | ............ A45D 40/0075 132/314 |
| 2019/0201926 A1 | 7/2019 | Corona et al. | |
| 2020/0002152 A1 | 1/2020 | Beyda et al. | |

FOREIGN PATENT DOCUMENTS

| | | |
|---|---|---|
| WO | WO 2012/018999 A1 | 2/2012 |
| WO | WO 2017/095854 A1 | 6/2017 |
| WO | WO 2018/169823 A1 | 9/2018 |
| WO | WO 2018/211253 A1 | 11/2018 |

OTHER PUBLICATIONS

Search Report issued in FR application No. 20000948, dated Oct. 19, 2020.

* cited by examiner

DEVICE FOR DISPENSING A FORMULATION OF AT LEAST TWO COMPOUNDS SELECTED FROM A SET OF SELECTABLE COMPOUNDS AND ASSOCIATED CONTAINER

TECHNICAL BACKGROUND

The invention concerns a device for dispensing a formulation of at least two compounds selected from a set of selectable compounds.

The different containers integrating these selectable compounds may appear in the form of interchangeable containers enabling to resupply the selectable compounds of the dispensing device. Thus, the invention also concerns a container associated with the dispensing device.

The invention may be implemented in a large number of fields for which it is desired to obtain a formulation based on different possible compounds.

The invention particularly advantageously applies in the field of cosmetics where it is desired to be able to formulate a cream tailored for the needs for treatment of a user's skin.

STATE OF THE ART

Cosmetic products have evolved in the last years to specifically respond to the needs for treatment of a user's skin. For this purpose, a plurality of solutions now provide testing the physiological characteristics of a user's skin to guide him/her towards the purchase of a cream adapted to his/her needs. Instead of recommending the purchase of a standard cream, company IOMA® provides a solution called "IOMA In.Lab" enabling to test a user's physiological parameters in a store to formulate a tailor-made cream.

However, the physiological parameters of a user's skin may vary over time and it is desired to be able to formulate tailor-made treatments which vary over time according to the stress undergone by the user's skin. For this purpose, company IEVA® sells a "Twin. C" jewel intended to be worn by the user to measure, over time, the parameters of the user's environment. This "Twin.C" jewel enables to measure the outdoor or indoor pollution, the exposure to sun, the ambient noise, the luminosity, temperature and humidity, and the number of steps. With all this information, it is possible to recommend a health/wellness ritual adapted to each user and capable of varying over time. It is further possible to determine the formulation of a cream specifically adapted to a user's needs.

The forming of this cream may then be formulated in store, for example, with the "IOMA In.Lab" formula. To be more independent and responsive, this cream may also be made at home. For this purpose, several companies provide machines for formulating a tailor-made cosmetic product, for example, Romy®'s "HyLab" compounder or L'Oréal®'s "Custom D.O.S.E" solution having its machine described in patent WO 2017/95854.

To generate his/her tailor-made cream, the user has a number of capsules containing the compounds of the different creams that he/she can formulate from the machine. During the cream manufacturing, the machine extracts the desired quantities of the compounds present in the different capsules inserted in the machine. The machine then mixes the extracted compounds to obtain a cream having an aspect corresponding to a standard cream but having its compounds and their quantities determined to measure.

This type of solution is however very difficult to transport since, as a coffee machine, this machine requires an electric power supply and a large number of electromechanical actuators to obtain the desired formulation, and particularly to mix the compounds.

Further, the use of capsules to integrate the different compounds capable of being used to obtain the formulation results in constraints of storage and pollution generated by the waste of the used capsules.

The technical problem of the invention is to obtain a formulation of at least two compounds selected from among a set of selectable compounds in a much more transportable way than existing solutions.

SUMMARY

To solve this technical problem, the invention provides a dispensing device enabling to extract compounds stored in containers to feed them to a dispensing surface. Thus, instead of completely forming a cream with the necessary mixing step, the invention provides delivering a desired quantity of the formulation for each application.

By delivering the compounds on the dispensing surface, the user may then recover the compounds with his/her finger to apply the formulation on his/her skin. The user's finger recovering the components thus achieves the association of the compounds.

The invention thus originates from a discovery according to which the active principles of a cream do not result from the conventionally performed mixing step but from the compounds taken independently. Thus, a simple association of the compounds, performed with a user's finger, is sufficient to obtain the same effects on the skin.

For this purpose, according to a first aspect, the invention concerns a device of distribution of a formulation of at least two compounds selected from a set of selectable compounds, said device comprising:

a plurality of containers storing said different selectable compounds;
 pumping means associated with each container;
 a dispensing surface comprising at least two through openings intended to deliver at least two selected compounds;
 selection means enabling to connect said at least two through openings to said means for pumping said selected compounds and to close the other pumping means; and
 an actuator configured to activate all of said pumping means and to only deliver said at least two selected compounds onto said dispensing surface.

The invention thus enables to deliver, on a dispensing surface, a specific formulation obtained from a set of selectable compounds. Thereby, the invention enables a user to form a dose of a cream adapted to his/her needs.

Conversely to existing custom compounding machines which aim at manufacturing a full jar of cream, the invention provides only dispensing one or a plurality of doses necessary for one application, so that the device of the invention may be much more compact and transportable than existing compounding machines.

According to the invention, the pumping means may correspond to mechanically or electromechanically actuated pumps. In the case of electromechanical pumps, the dispensing device preferably integrates batteries and a card for controlling the electromechanical actuators integrated in the dispensing device to form a self-contained and compact dispensing device.

Preferably, the dispensing device comprises mechanical pumps for forming the pumping means to obtain a purely mechanical dispensing device. In this embodiment, said actuator preferably corresponds to a push button having its upper surface corresponding to said dispensing surface, said pumping means having a stroke greater than or equal to the stroke of the push button. Thus, the activation of the push button activates the pumps and enables to deliver the selected compounds on the dispensing surface.

The selection of the compounds may be performed by any mechanical or electromechanical means. Preferably, the selection means correspond to mechanical means which enable to displace the openings or the containers to modify the matching between the openings and the containers.

According to a first embodiment where the openings are fixed, at least one of said selection means corresponds to a barrel integrating a plurality of containers, a rotation of said barrel causing a modification of the matching between an opening and one of the containers integrated in said barrel.

According to a second embodiment where the containers are fixed, at least one of said selection means corresponds to a ring connected to said dispensing surface so that a rotation of said ring causes:
 a rotation of said dispensing surface;
 a displacement of an opening; and
 a modification of the connection between said opening and one of said pumping means.

These two embodiments enable to mechanically select the selected compounds to dispense the formulation. When the compounds are selected, the user may then simply activate the pumping means via the actuator to obtain the compounds of the formulation on the dispensing surface.

It is possible to inhibit the operation of the actuator to avoid possible false manipulations of the dispensing device. For this purpose, it is possible to use a protection cap, which, once in place, blocks the access to the actuator. According to this embodiment, said device comprises a removable protection cap configured to cover said dispensing surface and inhibit the activation of said actuator.

As concerns the compounds used by the dispensing device, they may vary according to the applications of the dispensing device. Preferably, said device comprises two different types of compounds stored in two different types of containers; said at least two compounds being selected to obtain a formulation of at least a first type of compounds and of at least a second type of compounds.

For example, said device comprises from one to three compounds of the first type and from six to eight compounds of the second type to enable to obtain a large number of possible formulations.

According to the applications, compounds of different natures may be used. For example, the invention may be implemented for the formulation of a cosmetic cream. In this embodiment, said first type of compounds may correspond to bases, for example, aqueous or oily bases, and said second type of compounds may correspond to serums.

For a cosmetic cream, a formulation conventionally comprises a base and a serum with a larger quantity of base than of serum. To obtain this volume difference with the dispensing device, the first containers have a greater volume than second containers and said pumping means associated with said first containers have a larger pumping volume than said pumping means associated with said second containers for a same activation of said actuator.

Preferably, said plurality of containers is integrated in at least one support having at least two removable portions to enable to replace or to fill at least one container. By replacing the containers according to his/her needs, a user may increase the number of possible formulations that he/she can form with said dispensing device of the invention by using containers with other compounds than those present in the dispensing device.

Further, the replacing of the containers also enables to increase the lifetime of the dispensing device by replacing or by filling the empty containers. The possibility of filling the emptied containers also limits the waste generated by the dispensing device of the invention, thus improving its ecological footprint.

According to a second aspect, the invention concerns a container for a dispensing device according to the first aspect of the invention, said container comprising:
 a hollow body substantially having the shape of a cylinder portion with, between a lower surface and an upper surface, two planar surfaces and a surface in the shape of a portion of a cylinder; and
 a pump, assembled on said upper surface, configured to extract a compound stored in said body;
 said surface in the shape of a portion of a cylinder having at least two housings intended to receive two cylindrical containers, each housing emerging onto said upper surface and substantially extending between half the height of said body and said upper surface.

BRIEF DESCRIPTION OF THE DRAWINGS

The way to implement the present invention, as well as the resulting advantages, will better appear from the following embodiments, provided as an indication but not limiting, based on the accompanying drawings, among which

FIG. 1 is a front view of a device for dispensing a formulation according to a first embodiment of the invention;

FIG. 2 shows an exploded perspective view of the dispensing device of FIG. 1;

FIG. 3 is a cross-section view of the dispensing device of FIG. 1;

FIG. 4 is a top view of a lower ring of the dispensing device of FIG. 1;

FIG. 5 is a perspective view of the lower ring of FIG. 4;

FIG. 6 is a perspective view of an upper ring of the dispensing device of FIG. 1;

FIG. 7 is a partial cross-section view of the dispensing device of FIG. 1;

FIG. 8 is a perspective view of a container adapted to the dispensing device of FIG. 1;

FIG. 9 is a front view of a device for dispensing a formulation according to a second embodiment of the invention;

FIG. 10 shows an exploded perspective view of the dispensing device of FIG. 9;

FIG. 11 is a cross-section view of the dispensing device of FIG. 9;

FIG. 12 is a perspective view of a lower barrel of the dispensing device of FIG. 9;

FIG. 13 is a perspective view of an upper barrel of the dispensing device of FIG. 9;

FIG. 14 is a top view of the upper barrel of FIG. 13;

FIG. 15 is a perspective bottom view of the dispensing surface of the dispensing device of FIG. 9; and FIG. 16 is a perspective top view of the dispensing surface of the dispensing device of FIG. 9.

DETAILED DESCRIPTION

In the following description, two different embodiments illustrate a fully mechanical dispensing device. As a variant, the invention may be implemented with electromechanical components.

Figure 1:
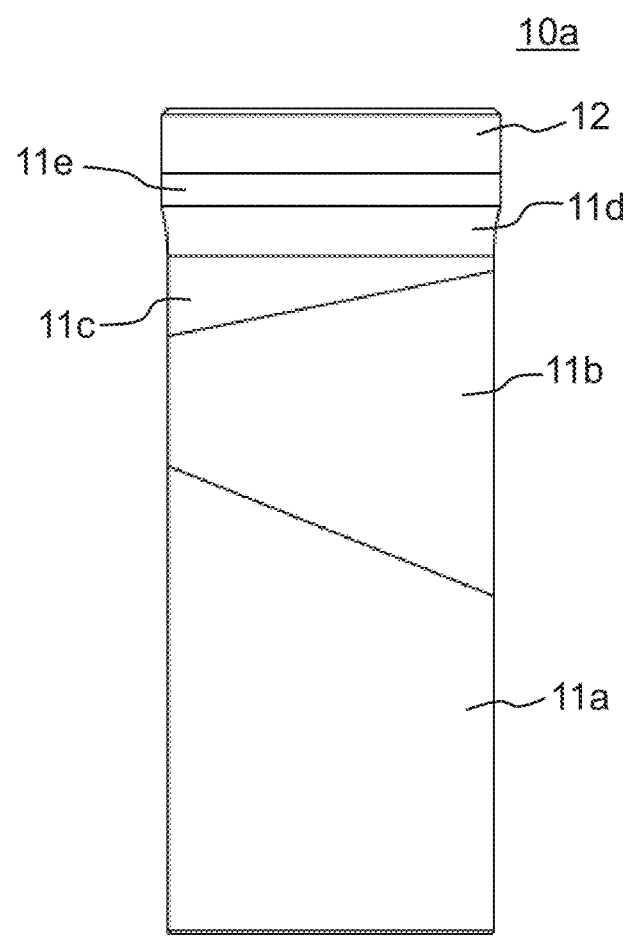
FIGS. 1 to 16 show.
Figure 2:
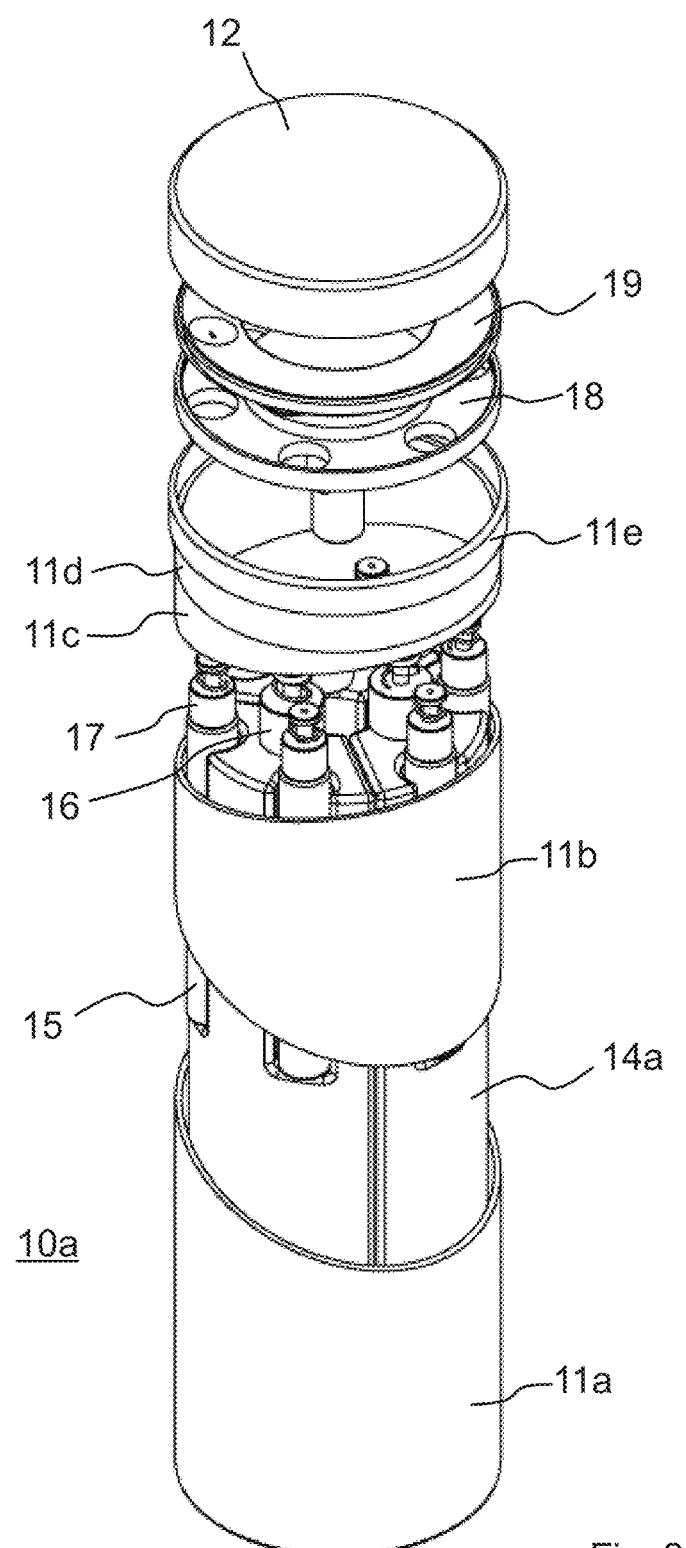
Figure 3:
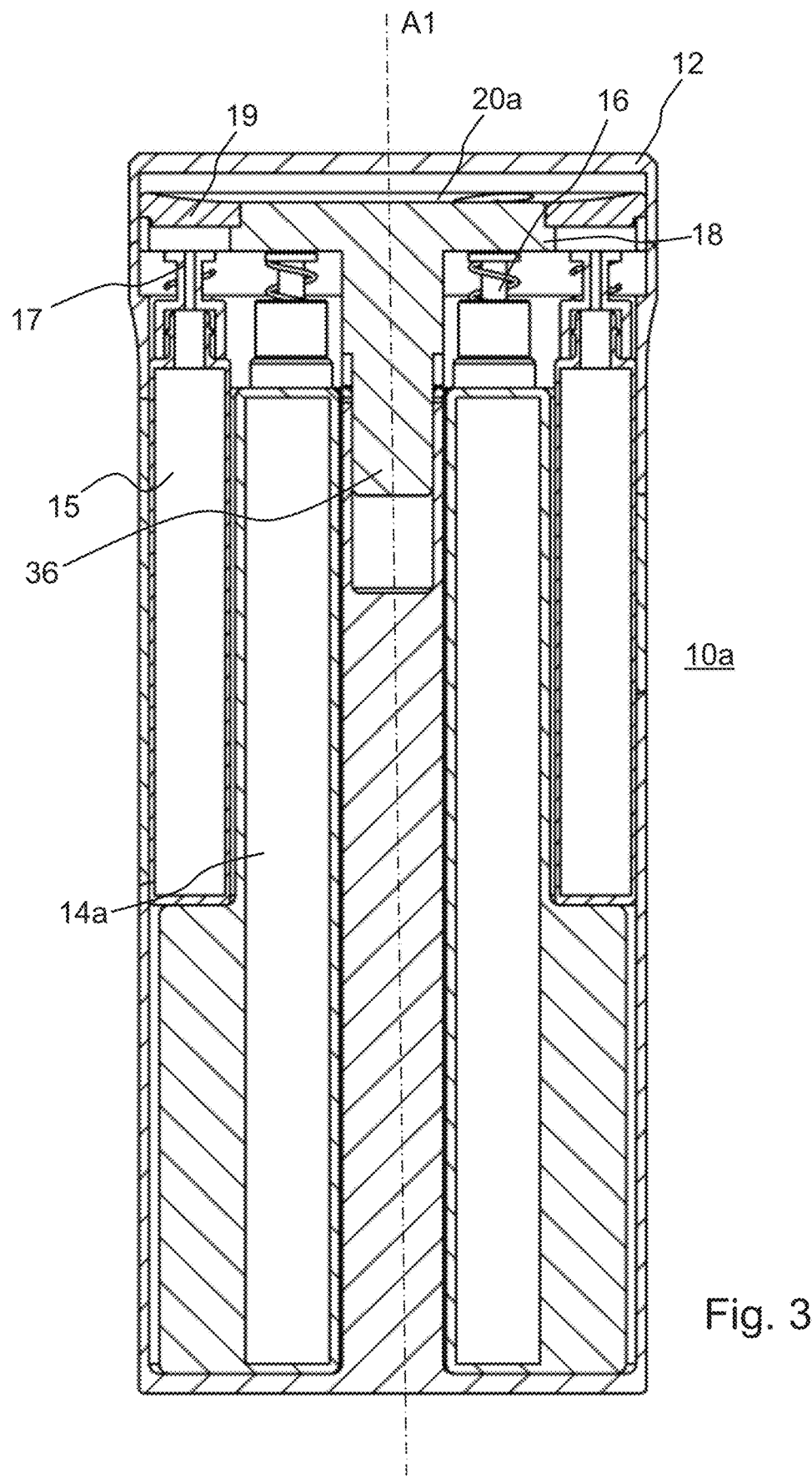

FIGS. 1 to 3 illustrate a dispensing device 10a according to a first embodiment of the invention. In this embodiment, dispensing device 10a has a substantially cylindrical shape with a height in the range from 7 to 15 cm and a diameter in the range from 3 to 10 cm.

Thus, dispensing device 10a appears in the form of a transportable vial.

Dispensing device 10a has an outer shell formed by a plurality of stacked portions 11a-11e attached to one another. The three lower portions 11a to 11c have complementary truncated cylindrical shapes enabling to obtain a cylinder integrating the different selectable compounds. The assembly of the three lower portions 11a to 11c enables to vary the materials, the textures, or the colors of this cylinder. Above this cylinder, the shell has a shoulder 11d topped with a cylindrical edge 11e. Further, the different portions 11a-11e of the shell are removably assembled to be able to open the shell and replace or fill one of containers 14a, 15. Shoulder 11d and edge 11e enable to integrate pumping means 16-17 and selection means 18-19.

Further, edge 11e is configured to support a protection cap 12 enabling to close dispensing device 10a. For example, protection cap 12 may be assembled by snapping or by screwing on edge 11e.

Inside of dispensing device 10a, the different selectable compounds are integrated in containers 14a-15. The selectable compounds may be dispensed in containers of large volume 14a integrating base compounds and containers of small volume 15 integrating serums enabling to formulate a cosmetic cream. For example, containers 14a have a volume in the range from 20 to 35 ml while containers 15 have a volume in the range from 3 to 8 ml.

Of course, other types of compounds may be used to obtain other formulations without changing the invention.

The extraction of the compounds stored in containers 14a-15 is preferably performed by a manual pump 16 or 17 associated with each container 14a-15.

A manual pump may suck in the compounds through a feed pipe extending down to the bottom of the container. Preferably, a plunger is integrated in each container 14a-15 so that a pressure applied on its pump 16-17 causes a depression which tends to displace the plunger towards the top of the container to extract the compound through an opening formed at the top of pump 16-17.

To obtain the desired formulation, dispensing device 10a enables to deliver the selected compounds onto a dispensing surface 20a so that a user can collect it with his/her finger. To form the selection means, the embodiment of FIGS. 1 to 8 provides using two concentric rings 18-19 forming at the same time dispensing surface 20a, the means of selection of the selected compounds, and an actuator for pumps 16-17. Ring 19 being assembled on ring 18, ring 18 is called "lower ring" while ring 19 is called "upper ring" in the rest of the description.

Figure 4:
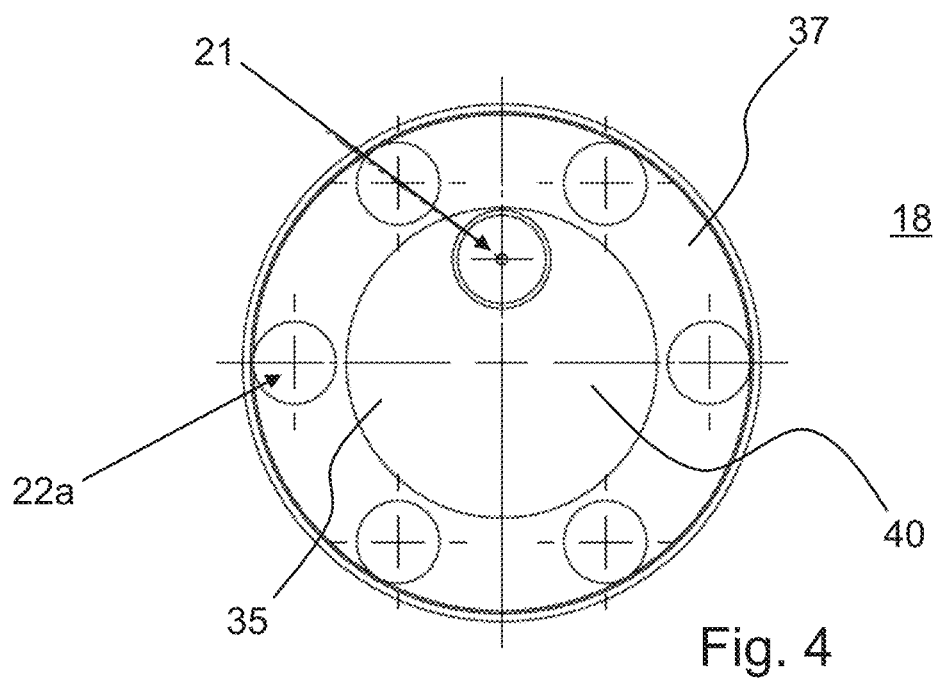
Figure 5:
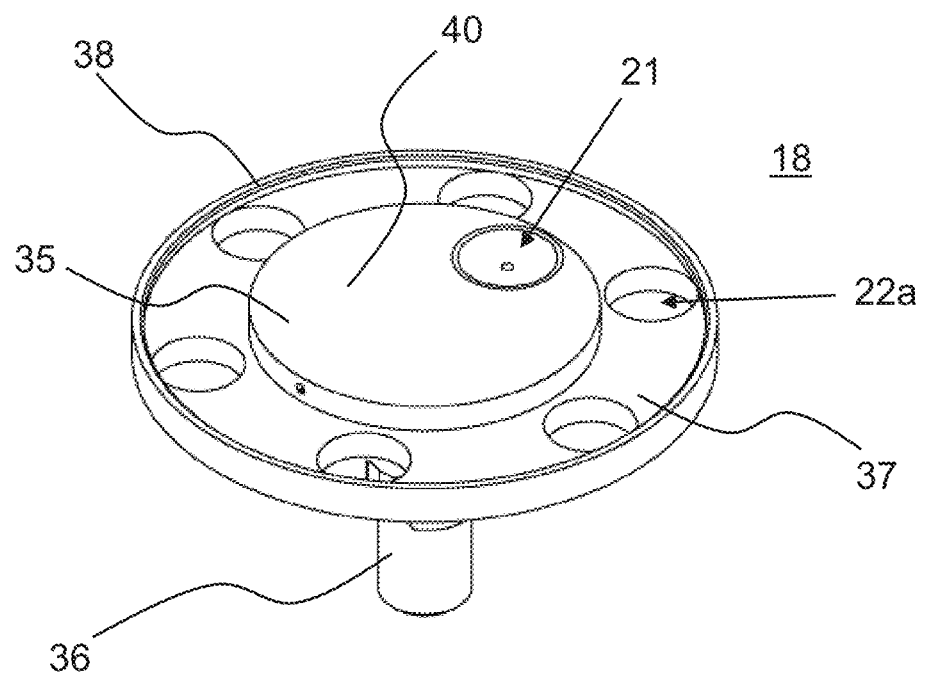

As illustrated in FIGS. 4 and 5, lower ring 18 has a central cylinder 35 having its lower surface provided with a guide pin 36. For example, central cylinder 35 may have a thickness in the range from 0.8 to 5 mm and a diameter in the range from 2 to 8 cm. The lower surface of lower ring 18 extends in the form of a disk 37 having a diameter greater than that of central cylinder 35. For example, disk 37 may have a thickness in the range from 0.4 to 2 mm and a diameter in the range from 3 to 10 cm. The terminal portion of disk 37 has an edge 38 orthoradially extending towards the upper surface 40 of central cylinder 35. The height of this edge 38 may be in the range from 0.2 to 2 mm.

Central cylinder 35 has a cylindrical opening 21 emerging onto the two upper 40 and lower surfaces and formed close to the edges of central cylinder 35. Cylindrical opening 21 may have a diameter in the range from 0.4 to 2 mm. Further, six other openings 22a are regularly distributed in disk 37. These other cylindrical openings 22a may also have a diameter in the range from 0.4 to 2 mm.

Figure 6:
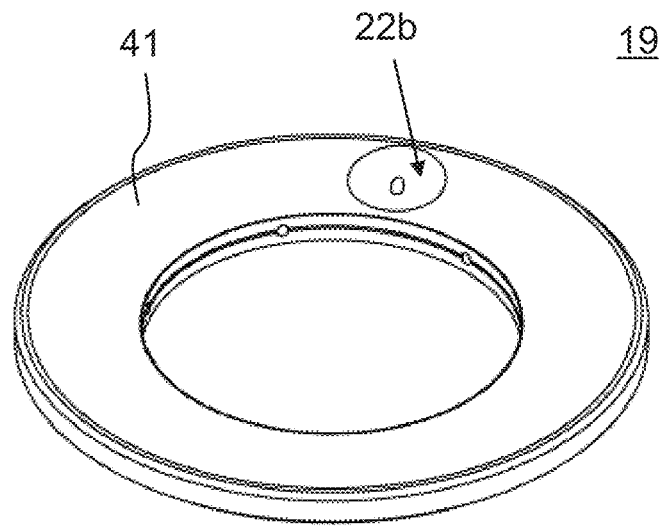

As illustrated in FIG. 6, upper ring 19 appears in the form of a ring 19. This ring 19 may have an inner diameter in the range from 2 to 8 cm and an outer diameter in the range from 3 to 10 cm. The thickness of ring 19 is preferably in the range from 0.4 to 2 mm. A through cylindrical opening 22b is formed across the thickness of this ring 19. Opening 22b may have a diameter in the range from 0.4 to 2 mm.

Figure 7:
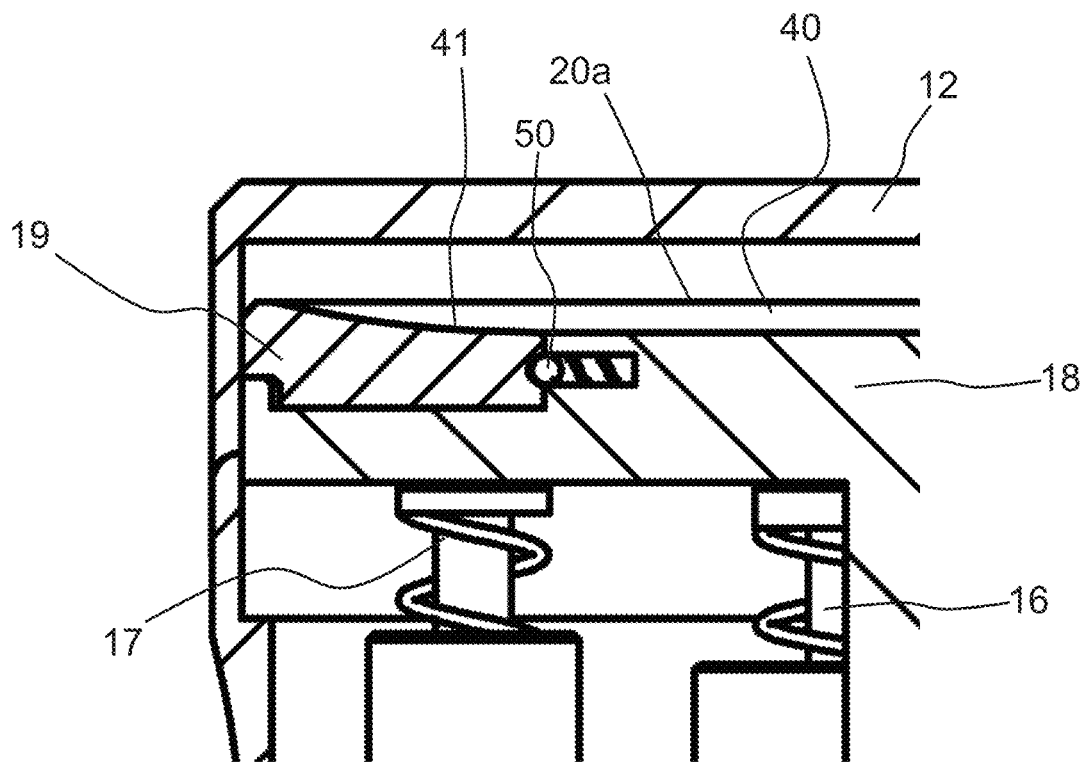

As illustrated in FIG. 7, dispensing surface 20a is obtained by the two upper surfaces 40-41 of the two rings 18-19. These two upper surfaces 40-41 are substantially coplanar when the upper ring 19 is assembled around the lower ring 18. Thus, the center of dispensing surface 20a is formed by the upper surface 40 of lower ring 18 running through upper ring 19 while the contour of dispensing surface 20a is formed by the upper surface 41 of lower ring 18.

To select the compounds and deliver them on dispensing surface 20a, the two rings 18-19 are rotatable around a central axis A1. Preferably, rings 18-19 can only be rotated when protection ring 12 is removed from dispensing device 10a.

Lower ring 18 is directly assembled above the assembly of pumps 16-17 and its through opening 21 enables to deliver a compound present in a container 14a onto its upper surface 40, that is, onto dispensing surface 20a. The feeding of a compound present in a container 15 is performed by crossing the openings 22a of lower ring 18 and the opening 22b of upper ring 19.

The activation of pumps 16-17 is obtained by the displacement of the two rings 18-19. For this purpose, the two rings 18-19 are laid on pump assembly 16-17 and pin 36 ensures the guiding of the displacement of the two rings 18-19.

Further, upper ring 19 is dished on lower ring 18 at the level of edge 38 so that the two rings 18-19 are jointly mobile along axis A1. The displacement of the two rings 18-19 is consecutive to a pressing by a user on dispensing surface 20a. This pressing results in compressing all pumps 16-17 and in causing a dispensing of the formulation of the selected compounds. Indeed, on activation of pumps 16-17, only the pumps arranged in front of openings 21 and 22b see their compounds fed to dispensing surface 20a. After the activation, that is, after the pressing by the user, the two rings 18-19 are repositioned in their initial positions by the decompression of the springs of pumps 16-17.

To ease the selection of the different compounds and to avoid for one of openings 21 and 22b to end up arranged between two pumps 16-17, positioning lugs are preferably implemented. For example, FIG. 7 illustrates a lug 50 and a spring integrated in a bore of lower ring 18 and configured to cooperate with bores present at each possible position of upper ring 19. Thus, the user may feel a difference of rotation effort of upper ring 19 between the possible positions and the intermediate positions of ring 19.

This embodiment, illustrated in FIGS. 1 to 7, may be implemented whatever the shape of the containers. For example, the invention may be implemented with standard containers having a cylindrical shape.

Preferably, to optimize the space inside of shell 11a-11e, the large volume container 14a has a specific shape enabling both to contain a compound and to integrate housings 30 therein to position cylindrical containers 15 of smaller volume.

Figure 8:
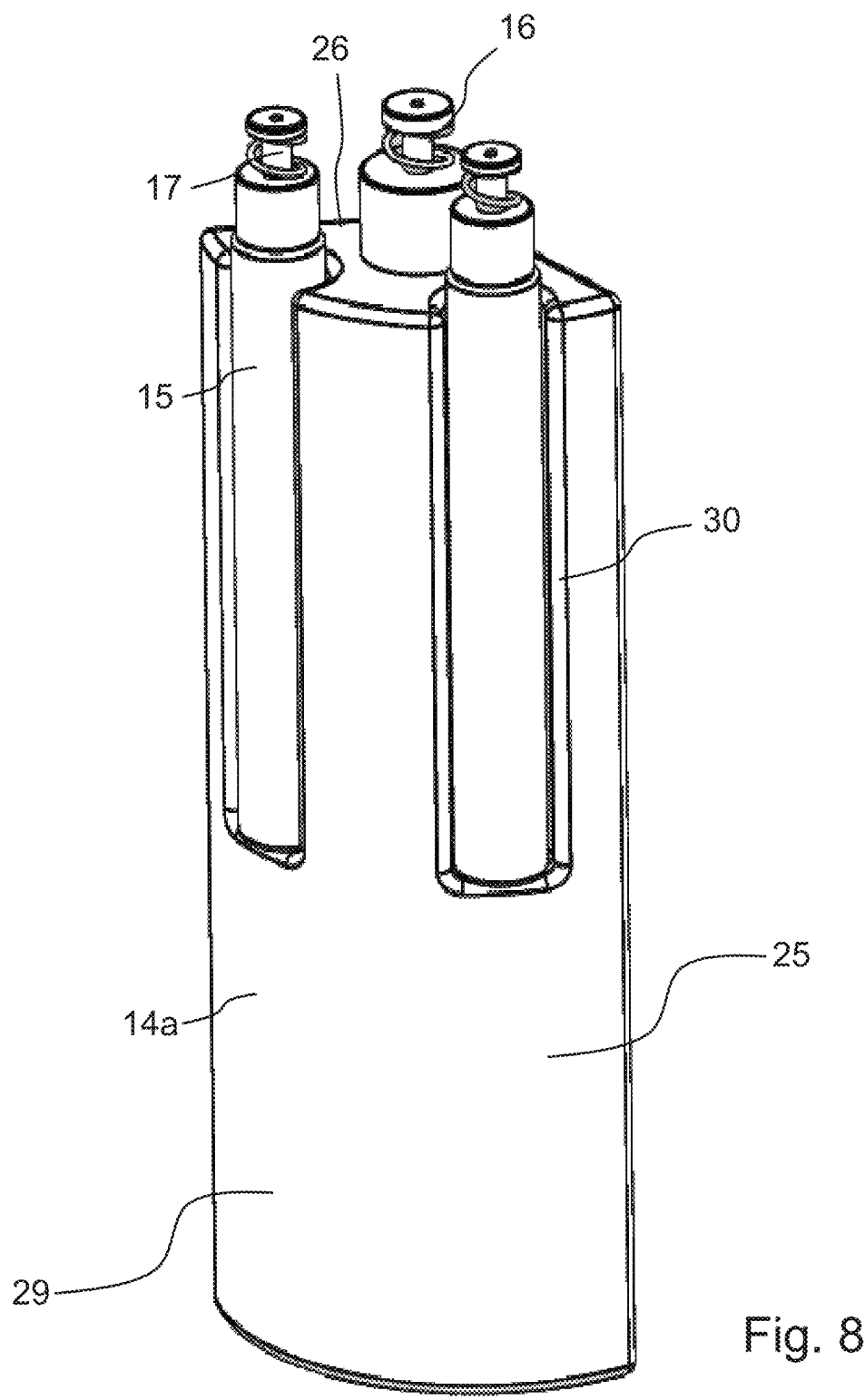
Figure 9:
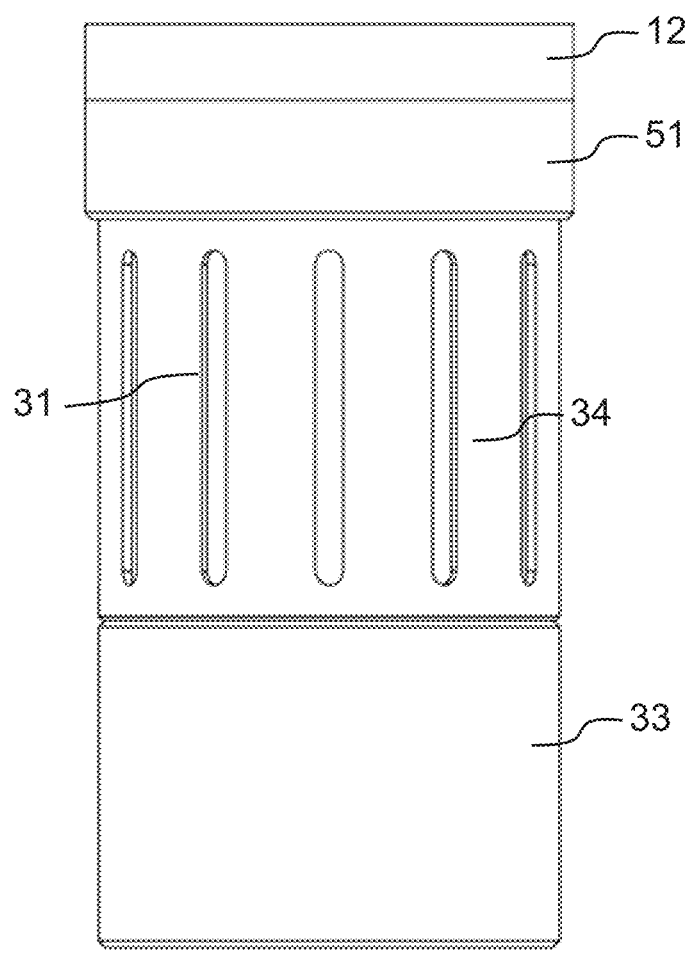
Figure 10:
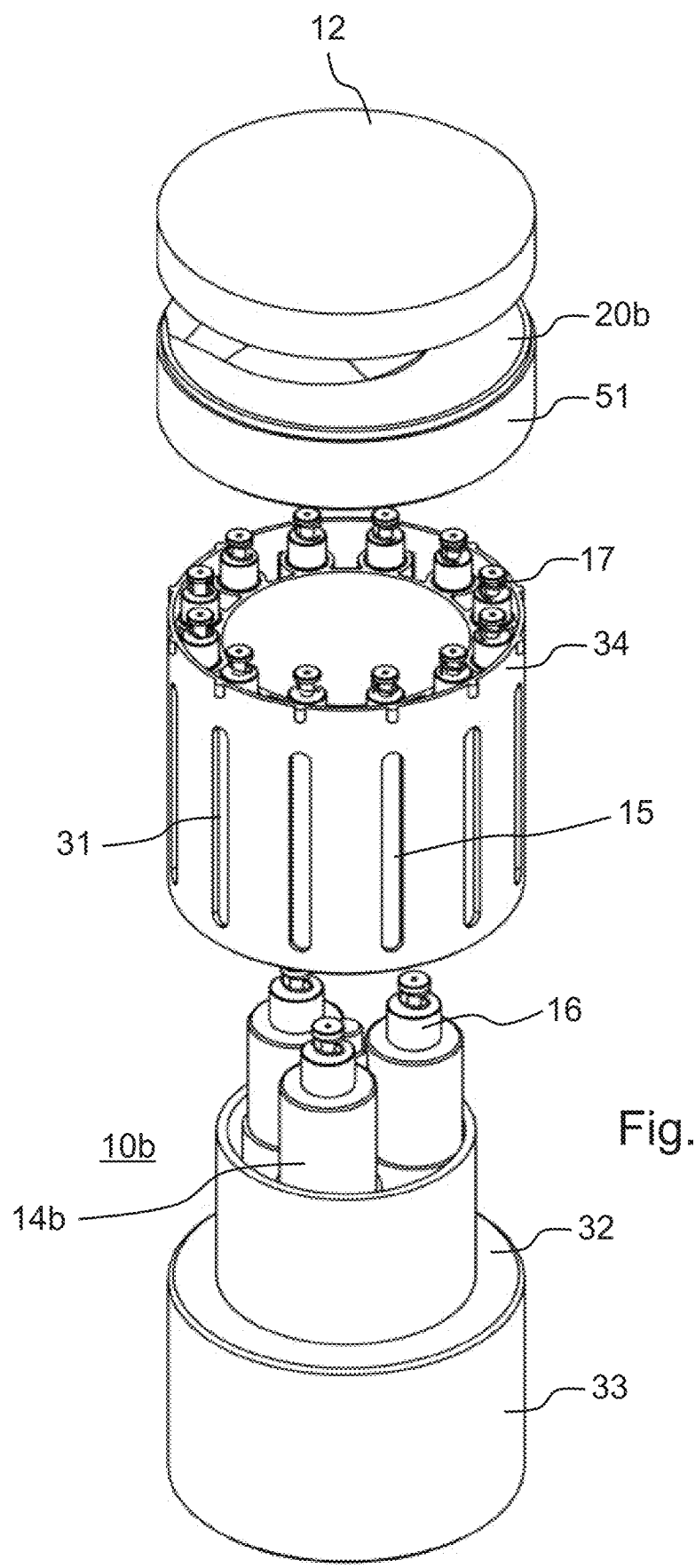
Figure 11:
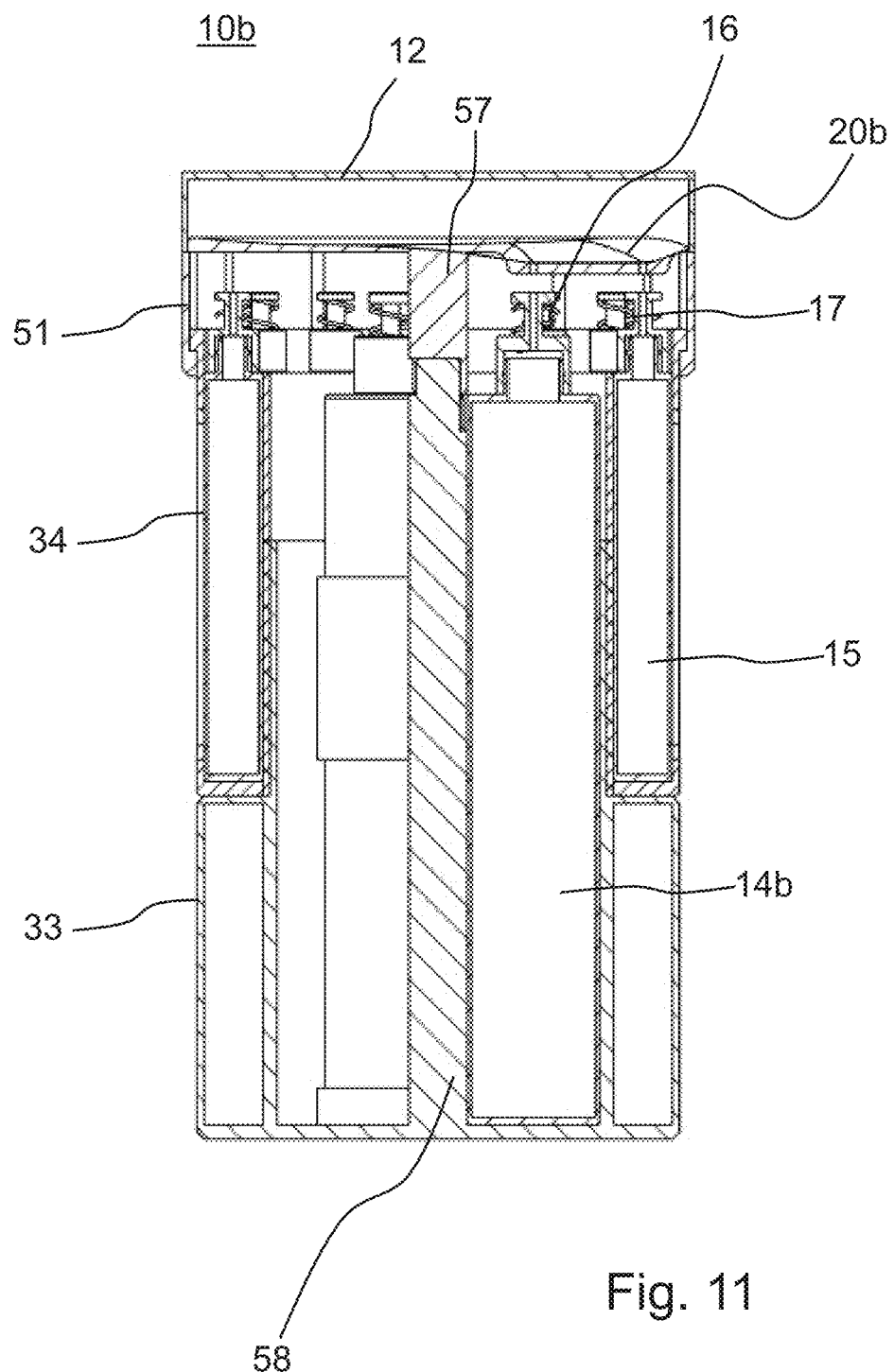
Figure 12:
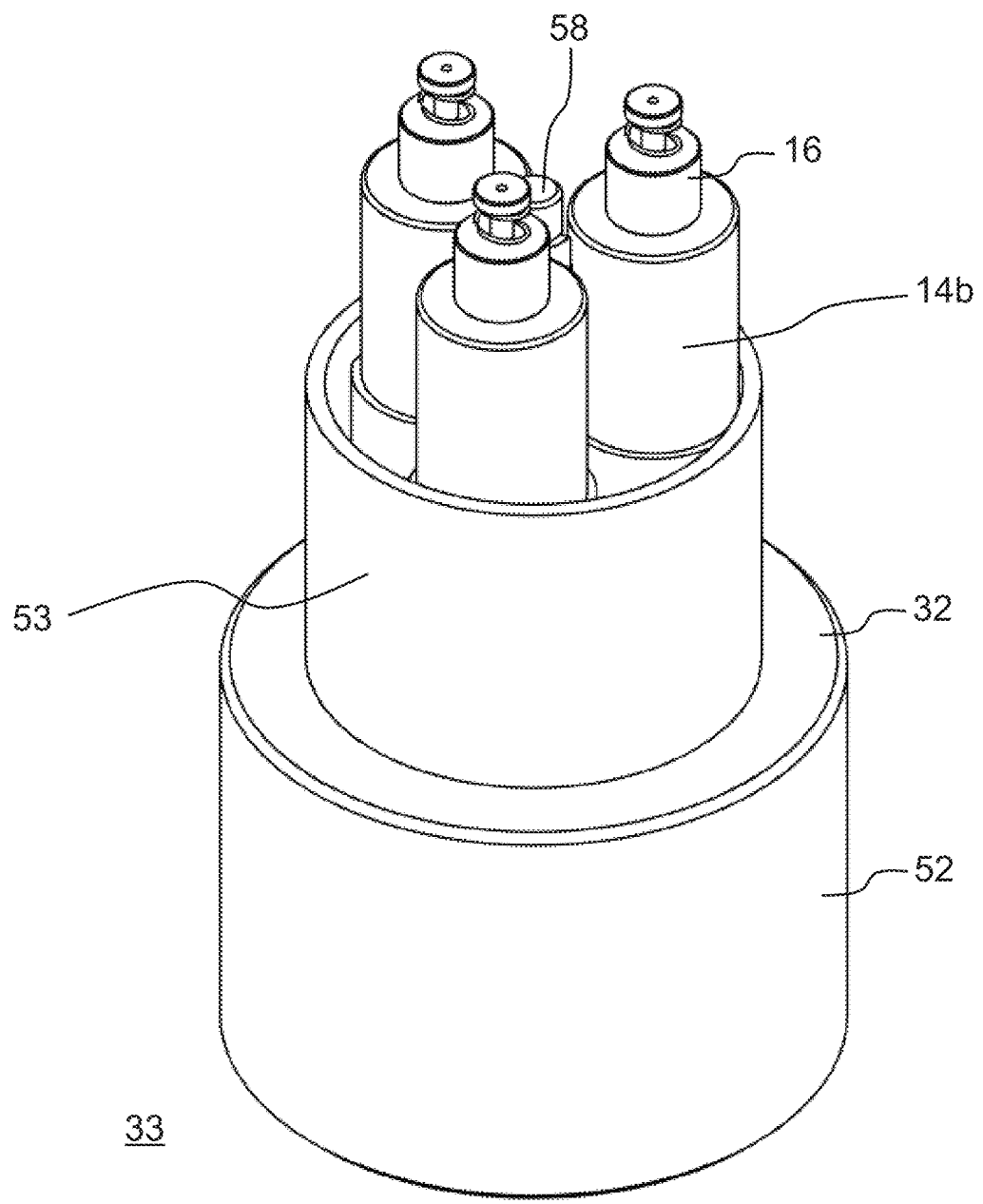
Figure 13:
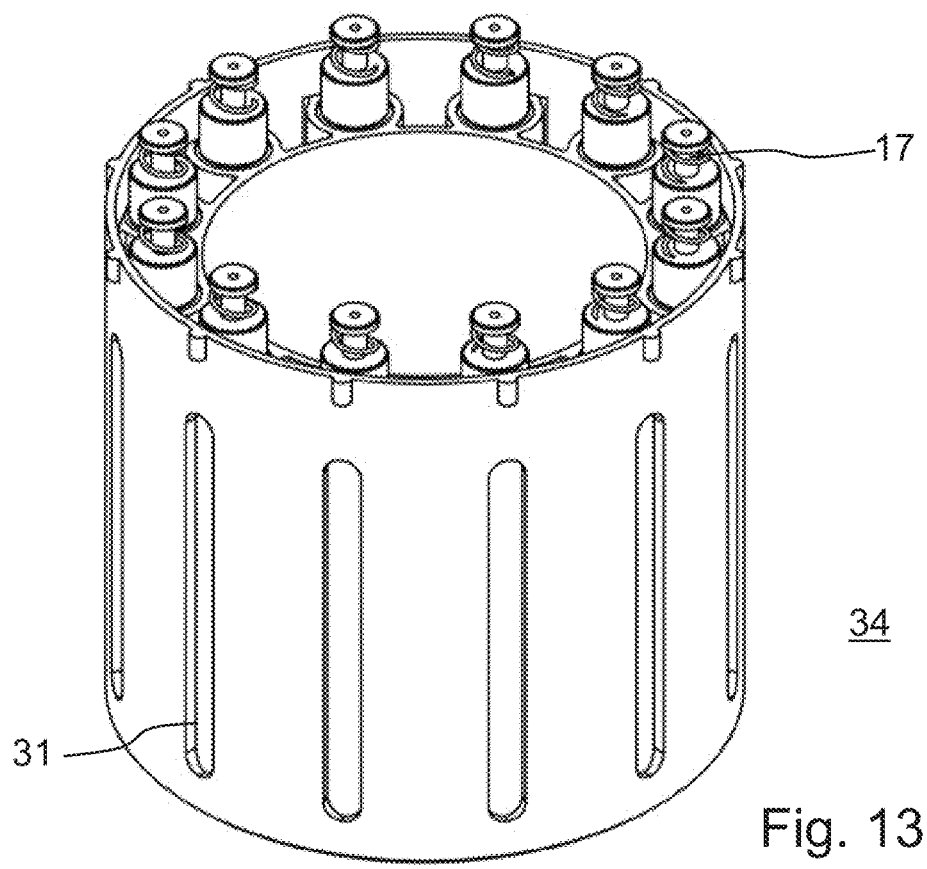
Figure 14:
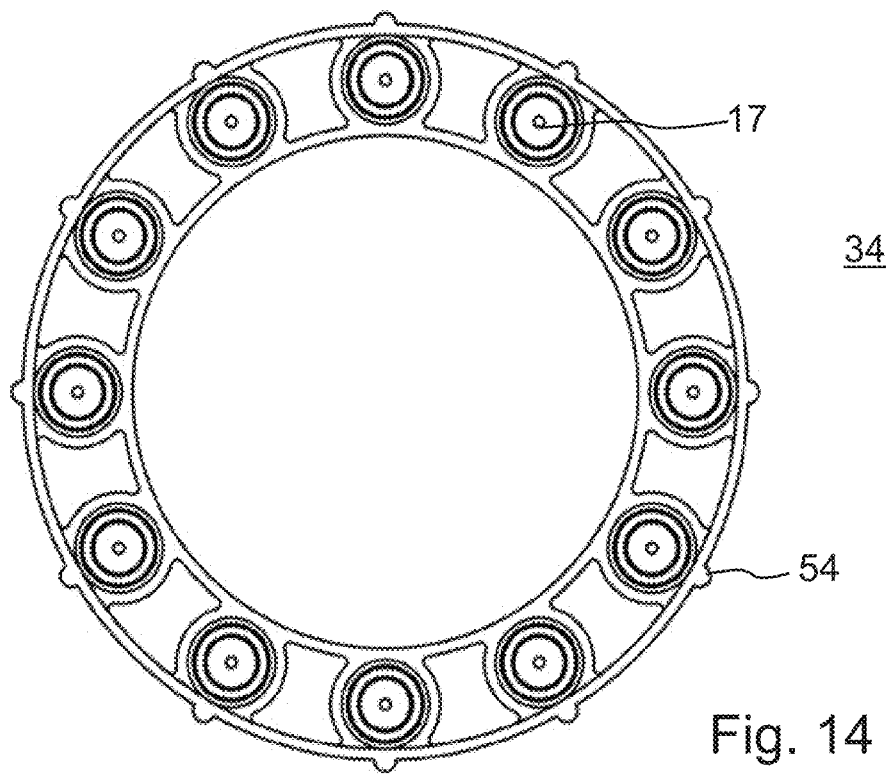
Figure 15:
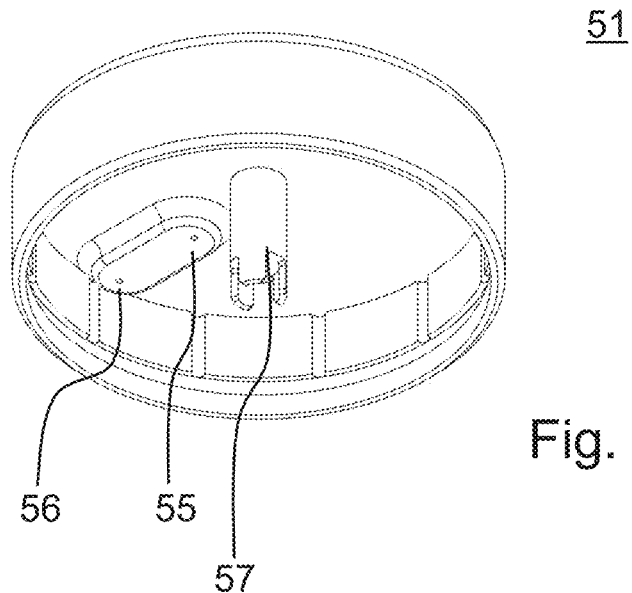

As illustrated in FIG. 8, container 14a has a hollow body 25 substantially having the shape of a cylinder portion with two planar surfaces and a curved surface 29 in the shape of a portion of a cylinder, extending throughout the height of the cylinder portion.

The lower surface of body 25 has a substantially planar surface while the upper surface 26 of body 25 integrates a pump 16 enabling to extract the compound stored in body 25. Further, the curved surface 29 has two housings 30 emerging onto upper surface 26 extending substantially between half the height of body 25 and upper surface 26.

In addition to the use of rings 18-19 to select the compounds of the formulation, it is also possible to use one or a plurality of cylinders 33-34 to replace one of rings 18-19. It is further possible to select more than two compounds by increasing the number of selection means. Further, by using three rings, it is possible to select three different compounds to dispense a formulation. The selection means may also have an intermediate position between a plurality of containers where no compound is delivered so that it is possible to deliver a single compound by positioning one of the selection means in this intermediate position.

FIGS. 9 to 16 illustrate a second embodiment using two barrels 33-34 to select the compounds. In the same way as in the first embodiment, a dispensing surface 20b is arranged opposite an assembly of pumps 16-17 assembled on containers 14b-15. However, this dispensing surface 20b is fixed and containers 14b-15 are mobile with respect to this dispensing surface 20b.

For this purpose, dispensing device 20b has a first barrel 33 comprising a lower cylinder 52 and an upper cylinder 53 of smaller diameter forming a shoulder 32. Three cylindrical containers 14b are inserted in the two cylinders and protrude upwards.

Shoulder 32 enables to assemble a second barrel 34 taking the shape of a hollow cylinder supporting twelve containers 15.

A dispensing cap 51 is fixedly assembled above the two barrels 33-34. This dispensing cap 51 has a shaft 57 assembled on a central shaft 58 of the first barrel 33 so that the shaft 58 of the first barrel 33 is rotatable with respect to the shaft 57 of dispensing cap 51.

Second barrel 34 is locked in translation between shoulder 32 and dispensing cap 51 so that this second barrel 34 is rotatable around shafts 57-58, independently from the rotations of first barrel 33. As illustrated in FIG. 4, the upper end of second barrel 33 may comprise lugs 54 to form positioning lugs with respect to dispensing surface 20b.

First barrel 33 is removably assembled on shaft 57 so that the two barrels can be disassembled to replaced or fill one of containers 14b, 15. Further, the level of containers 15 may be directly visible for openings 31.

Figure 16:
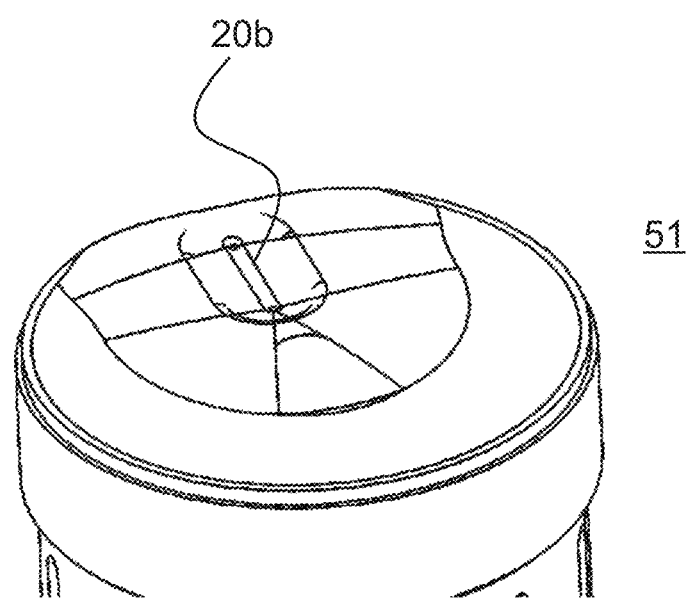

In dispensing cap 51, two openings 55 and 56 are formed to enable the pumps 16-17 arranged at the surface of these openings 55-56 to feed their contents onto dispensing surface 20b. Further, openings 55 and 56 being fixed, dispensing surface 20b may be structured to ease the grabbing of the compounds by the user, as illustrated in FIG. 16. In the same way as for the first embodiment, the actuation of pumps 16-17 may be performed by displacing dispensing surface 20b.

The invention thus enables to obtain a device for dispensing a formulation of at least two compounds selected from a set of selectable compounds, which is much more transportable than existing solutions. Further, this dispensing device may be fully mechanical.

Thus, a user may rapidly and simply formulate a tailor-made formulation according to his/her needs. For example, with the invention, a user may formulate one or a plurality of doses of a cosmetic cream adapted to treating his/her skin.

What is claimed is:

1. A device for dispensing a formulation of at least two compounds selected from a set of selectable compounds, said device comprising:
    a plurality of containers storing the different selectable compounds;
    a pump associated with each container;
    a dispensing surface comprising at least two through openings configured to deliver at least two selected compounds;
    a selector configured to connect said at least two through openings to said pumps associated with said selected compounds and to close the other pumps, wherein said selector corresponds to a barrel integrating the plurality of containers, a rotation of said barrel causing a modification of the matching between an opening and one of the containers integrated in said barrel; and
    an actuator configured to activate each of said pumps and only deliver said at least two selected compounds onto said dispensing surface.

2. The dispensing device according to claim 1, wherein said actuator corresponds to a push button having its upper surface corresponding to said dispensing surface, said pump having a stroke greater than or equal to the stroke of the push button.

3. The dispensing device according to claim 1, wherein said selector corresponds to a ring connected to said dispensing surface so that a rotation of said ring causes:
    a rotation of said dispensing surface;
    a displacement of an opening; and
    a modification of the connection between said opening and one of said pump.

4. The dispensing device according to claim 1, wherein said device comprises a removable protection cap configured to cover said dispensing surface and inhibit the activation of said actuator.

5. The dispensing device according to claim 1, wherein said device comprises two different types of compounds stored in two different types of containers; said at least two compounds being selected to obtain a formulation of at least a first type of compounds and of at least a second type of compounds.

6. The dispensing device according to claim 5, wherein first containers have a greater volume than second containers; said pump associated with said first containers have a much larger pumping volume than said pump associated with said second containers for a same activation of said actuator.

7. The dispensing device according to claim 5, wherein said device comprises between one and three compounds of the first type and between six and eight compounds of the second type.

8. The dispensing device according to claim 5, wherein said formulation corresponding to a cosmetic cream, said first type of compounds corresponds to bases and said second type of compounds corresponds to serums.

9. The dispensing device according to claim 1, wherein said plurality of containers is integrated in at least one support having at least two removable portions to enable to replace or to fill at least one container.

10. A container for the dispensing device according to claim 1, said container comprising:
- a hollow body substantially having the shape of a cylinder portion with, between a lower surface and an upper surface, two planar surfaces planes and one surface in the shape of a portion of a cylinder; and
- a pump, assembled on said upper surface, configured to extract a compound stored in said body;
- said surface in the shape of a portion of a cylinder having at least two housings intended to receive two cylindrical containers, each housing emerging onto said upper surface and substantially extending between half the height of said body and said upper surface.

* * * * *

UNITED STATES PATENT AND TRADEMARK OFFICE
CERTIFICATE OF CORRECTION

| | |
|---|---|
| PATENT NO. | : 11,730,252 B2 |
| APPLICATION NO. | : 17/162250 |
| DATED | : August 22, 2023 |
| INVENTOR(S) | : Cyril Clappaz |

It is certified that error appears in the above-identified patent and that said Letters Patent is hereby corrected as shown below:

On the Title Page

Item [72], Line 2, delete "Lyons" and insert -- Lyon --.

In the Claims

Column 8, Line 53, Claim 6, before "larger" delete "much".

Signed and Sealed this
Fourteenth Day of November, 2023

*Katherine Kelly Vidal*
Katherine Kelly Vidal
*Director of the United States Patent and Trademark Office*